United States Patent
Thompson

[19]

[11] Patent Number: 5,669,395
[45] Date of Patent: Sep. 23, 1997

[54] DISPOSABLE PROTECTIVE WEAR FOR SUN TANNING

[76] Inventor: Yvonne Thompson, 237 Oakcrest La., Pittsburgh, Pa. 15236

[21] Appl. No.: 724,134

[22] Filed: Sep. 30, 1996

[51] Int. Cl.⁶ ........................................................ A61F 5/37
[52] U.S. Cl. .................... 128/846; 128/857; 128/858; 128/890
[58] Field of Search ........................ 128/845, 846, 128/849–856, 857, 858, 842, 844, 918; 250/516.1, 519.1; 2/2, 102

[56] References Cited

U.S. PATENT DOCUMENTS

| | | | |
|---|---|---|---|
| 2,432,767 | 12/1947 | Klein | 128/858 |
| 2,527,947 | 10/1950 | Loos | 128/163 |
| 2,851,805 | 9/1958 | Allen | 41/10 |
| 3,310,053 | 3/1967 | Greenwood | 128/846 |
| 3,619,815 | 11/1971 | Towner | 128/858 |
| 3,695,265 | 10/1972 | Brevik | 128/146.2 |
| 3,736,946 | 6/1973 | Yando et al. | 132/88.5 |
| 4,024,879 | 5/1977 | Stryker | 132/88.5 |
| 4,033,364 | 7/1977 | Ingana et al. | 132/88.5 |
| 4,383,539 | 5/1983 | Collins | 132/88.5 |
| 4,938,233 | 7/1990 | Orrison | 128/849 |
| 5,207,233 | 5/1993 | Barnes | 128/842 |

FOREIGN PATENT DOCUMENTS

| | | |
|---|---|---|
| 783924 | 4/1935 | France . |
| 1328522 | 4/1963 | France . |
| 1354100 | 1/1964 | France . |

*Primary Examiner*—Michael A. Brown
*Attorney, Agent, or Firm*—Kenneth P. McKay

[57] ABSTRACT

Disposable protective wear for persons who sun tan, providing a shield for sensitive parts of the body against exposure, while allowing for maximum coloring of the body and sanitary conditions within tanning salons. The disposable protective wear consists of separate articles of face cover, adjustable lower cover and breast covers, all with adhesive means to hold the articles in place on the wearer.

3 Claims, 6 Drawing Sheets

5,669,395

DISPOSABLE PROTECTIVE WEAR FOR SUN TANNING

BACKGROUND OF THE INVENTION

1. Field of the Invention

The invention relates to disposable protective wear for persons who sun tan, as a shield for sensitive parts of the body against exposure, while allowing for maximum coloring of the body and sanitary conditions within tanning salons.

2. Description of the Related Art

The current art shows a variety of sunbathing apparel, including clothing articles such as bathing suits and bikinis. In particular, with respect to sunbathing only, the prior art shows a variety of protectors and forms by which the sun may be used to tattoo the body. Other articles of apparel, such as face masks and false eyebrows, are used to compliment the dress of a user. Specialized use items such as eye makeup shields and tattoos are used for cosmetic tattooing. Processes include devices used to provide ornamental designs on the human body including ornaments for finger and toenails.

The use, commercially, of sun tanning beds is recent. Although the prior art teaches the use of sun tanning beds, it does not relate to apparel such as is presented by the current invention. There is, therefore, the expectation within the prior art that a person using a sun tanning bed either adapts beach wear, gym wear or street wear for use within the sun tanning bed, or is totally nude while so tanning.

A main drawback of the current art is that a person using a sun tanning bed, or other artificial light source for sunbathing, must bring their own bathing attire to use at the salons, parlors, gymnasiums, spas or other facilities which employ sun tanning beds. This is extremely inconvenient for the casual sun tanning bed user or the user who decides, on the spur of the moment, to use a sun tanning bed and has not brought their own articles of wear. It is unsanitary to use articles of clothing the user is wearing, both for the current and subsequent users. Another drawback is that articles of apparel worn for sunbathing at the beach cover a large portion of the body that a sun tanning bed user would not be so inclined to require, from the standpoint of modesty. In addition, the articles of apparel leave sunbathing lines which the sun tanning bed user does not desire.

A major drawback and fault of the prior art is that, considering the consumer nature of the sun tanning bed market, sanitation concerns are high when customers wear personal attire which touches the sun tanning bed surfaces, or when they use the beds while nude, which then must be used by another.

The current invention addresses each of those concerns, and solves them accordingly, at little cost and great convenience for sun tanning bed users.

PRIOR ART

U.S. Pat. No. 2,527,947 (Loos) shows eye protectors which shield eyes while a sunbath is taken.

U.S. Pat. No. 2,851,805 (Allen) shows the art of tattooing devices which cause a temporary tattoo on the human skin by shielding decorative patches of the skin from exposing sunlight, thereby leaving skin-colored tattoos against a darker background.

U.S. Pat. No. 3,695,265 (Brevik) shows a mask for removing particulate airborne matter during inhalation by means of a piece of patch which attaches to the nose of the user.

U.S. Pat. No. 3,736,946 (Yando et al) shows the art of ornamentation for applying designs to human fingernails or toenails.

U.S. Pat. No. 4,024,879 (Stryker) shows an eyebrow beauty kit of hair bearing flexible adhesive backed material for installing eyebrows on the person.

U.S. Pat. No. 4,033,364 (Inzana et al) discloses a shield for use in applying mascara to the eyelashes which prevents the smudging of eyeshadow and/or eyeliner.

U.S. Pat. No. 4,383,539 (Collins and Vota) shows a cosmetic preparation for applying a cosmetic powder onto the skin and being fixed in a specific design thereon.

Foreign Patent France 1.328.522 (Jozwiak) shows a masking means by which eyebrow liner and lipstick are applied by means of a template.

Foreign Patent France 1.354.100 (Culebra) shows a decorative tattooing template.

SUMMARY OF THE INVENTION

The objective of the present invention is to provide a disposable means of body shielding such that sanitation in the tanning area is maintained, at small cost to the individual users.

A second objective is to minimize the amount of covered area of the body in the shielding cover in order to maximize the tanned surfaces of the body.

A third objective is to allow for pleasant designs to be tanned into the body, especially around areas of the body which may be later exposed to other persons.

A fourth objective is to means of shielding sensitive body parts from the potentially harmful ultraviolet rays encountered in a tanning bed.

The Disposable Protective Wear For Sun Tanning comprises articles of temporary wear including a face mask, a lower cover and a pair of breast covers. The lower cover may be adapted for either a male or female form.

The invention, in its preferred embodiment, includes the articles described above, fabricated from light cloth, tissue or paper, and fastened to the body with small adhesive backed strips. The materials are very low cost, easily fabricated and thereby allow for disposable use. For simplicity, the face mask may be made without adhesive backed strips whereby the face masks merely rests on the person who is sunbathing while lying on their back.

DETAILED DESCRIPTION OF THE PREFERRED EMBODIMENT

Figure 1:
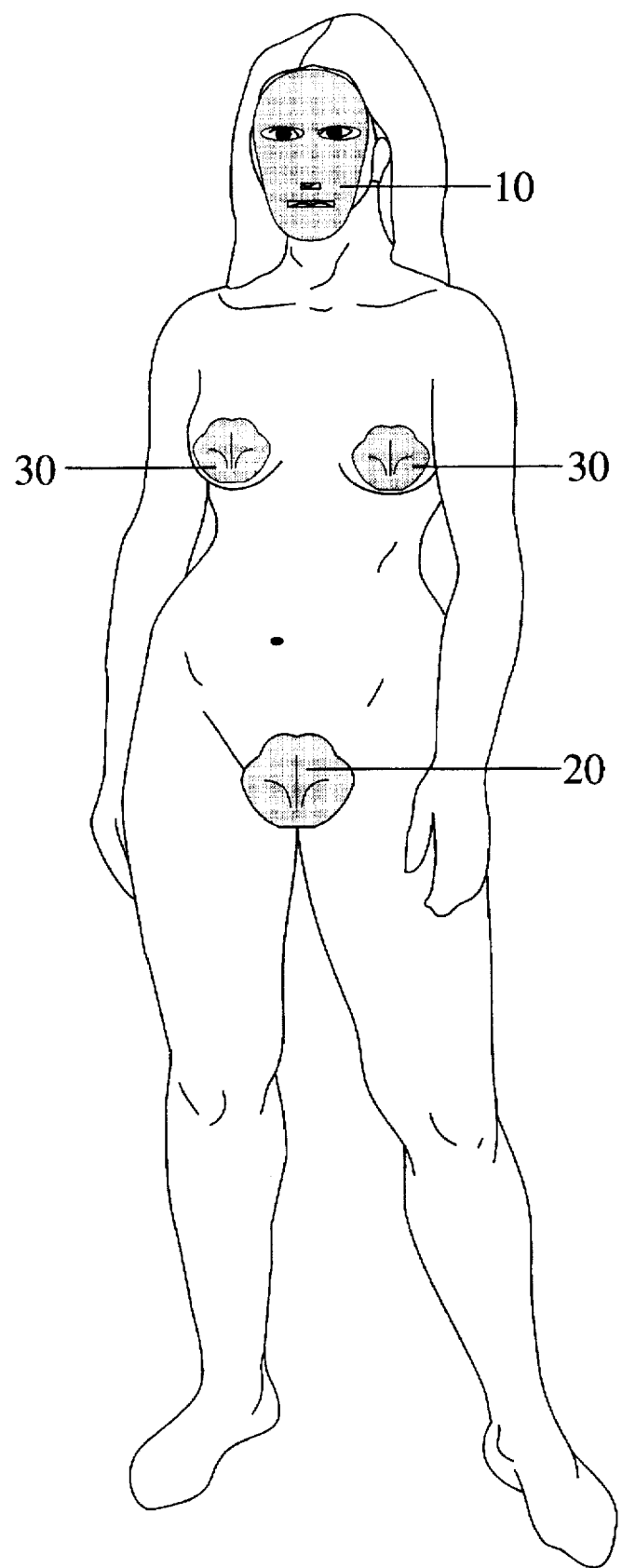
FIG. 1 is a perspective of the Disposable Protective Wear For Sun Tanning in a kit form which shows the protective face mask and protective emblems for the breast and genitalia area of a female.

FIG. 1 shows the subject invention, face mask, 10, for covering the wearer's face, lower cover 20 for covering the genitalia area and breast cover 30 for protecting the sensitive areas of the breast, particularly the nipples.

Figure 2:
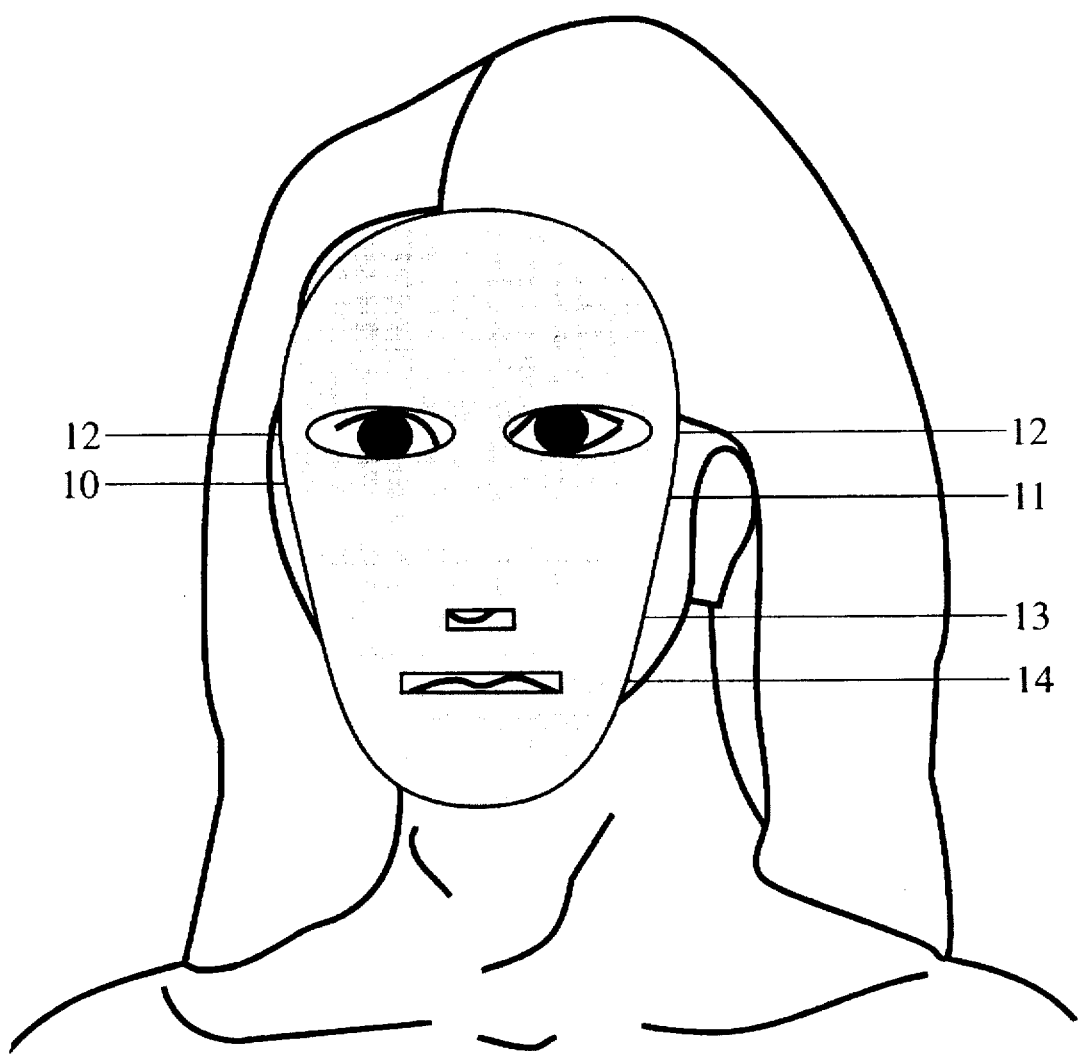
FIG. 2 is a view of the face mask.

FIG. 2 shows the face mask, 10. The face cover 11 is fabricated from a single panel cut to generally pattern the human face. Face cover 11 is made from a single or plurality of pieces of light-weight, white or lightly-colored material such as gauze, tissue or light paper. Assembly is performed by cutting the pattern, which may vary as may the materials selected for fabrication. The face cover 11 has fashioned with holes into which are placed eye piece viewing means 12, used to shield the wearer's eyes from ultraviolet rays present in sunlight. The eye piece viewing means 12 may be made from translucent or see-through colored plastic or colored paper, glued or otherwise connected to the internal surfaces of the face cover 11. Also fashioned within the face cover 11 are nose slit 13 and mouth slit 14, which provide a means for the wearer to readily breath while wearing the face mask 10. The nose slit 13 and mouth slit 14 are either cut into the face cover 10 or stamped out from the material during fabrication.

Figure 3:
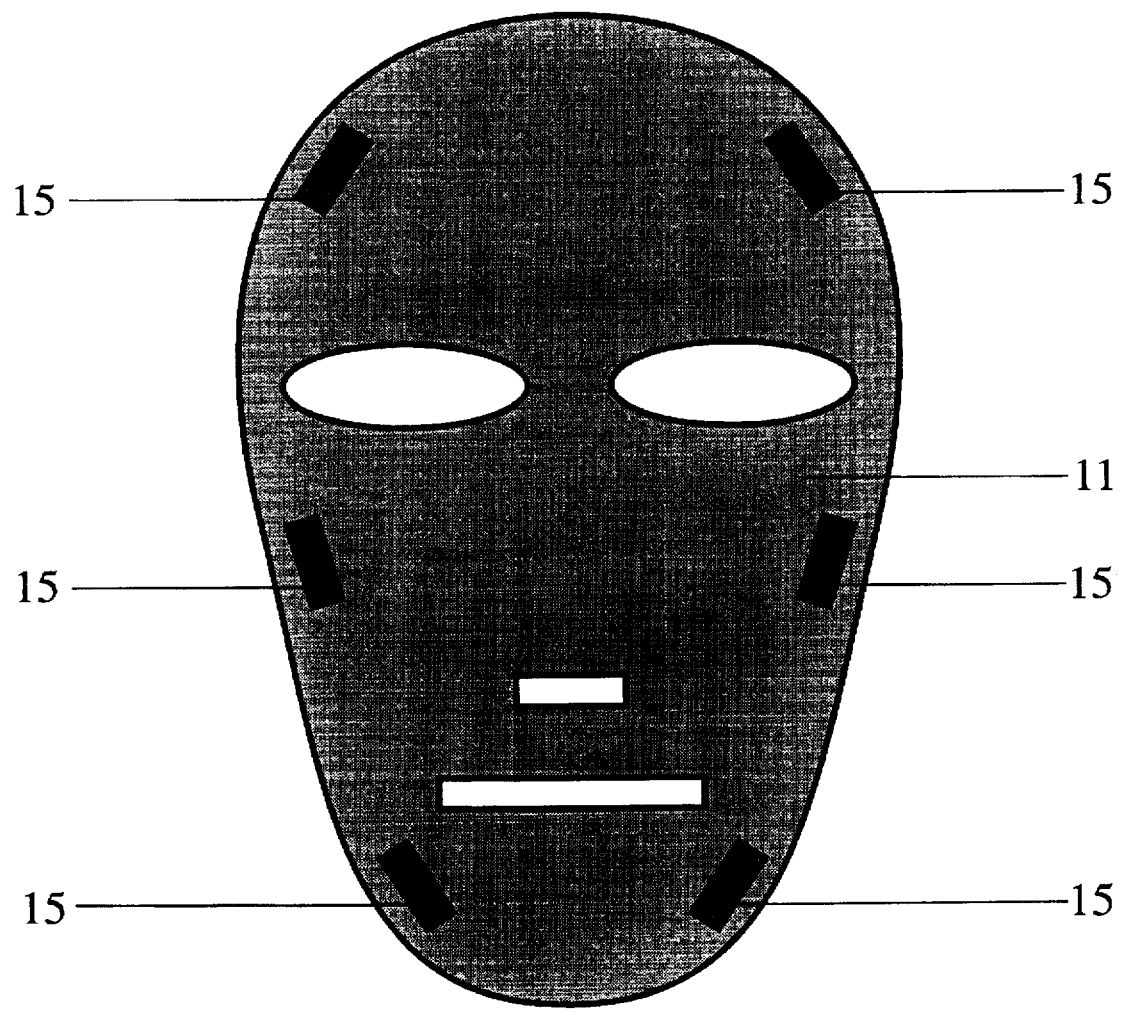
FIG. 3 is a view of the reverse side of the face mask showing the adhesive means used to secure the face mask to the user.

FIG. 3 shows the reverse side of the face cover 11. A multitude of small adhesive means 15 are applied to the reverse side of the face cover 11 to keep it in place on the wearer, if the wearer so chooses. In the preferred embodiment, the small adhesive means are double adhesive backed tape which allows the wearer to peel a protective cover from the exposed surface which then gently adhere to the skin of the wearer. The adhesive is water insoluble to resist dissolution in humid or damp environs.

Figure 4:
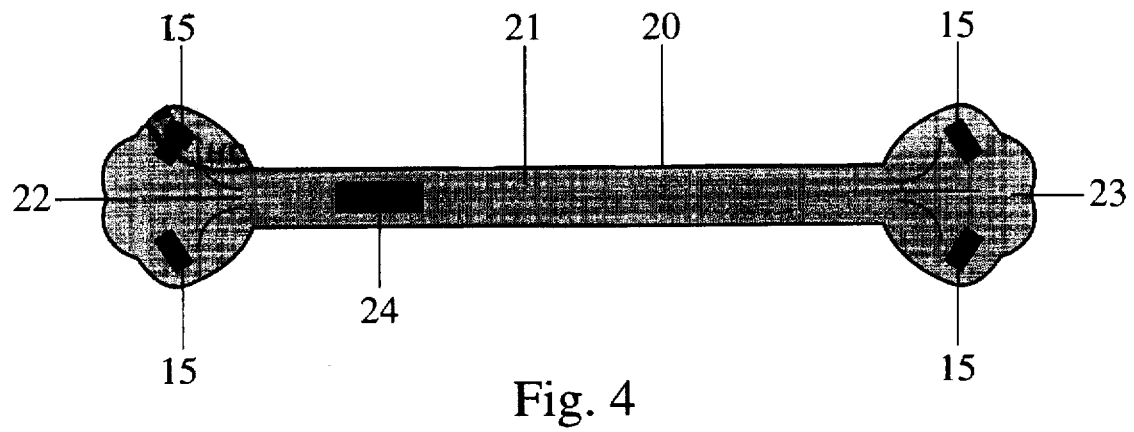
FIG. 4 shows the protective piece used to protect the genitalia area of a female.

FIG. 4 shows the lower cover 20 in reverse view. The lower cover 20 is comprised of a length portion 21, a front emblem 22 and a rear emblem 23 which is fashioned from a single or multitude of pieces of fabric paper or cloth in such a manner as to allow the length portion 21 to be strung through the crotch of the wearer and be fastened to the front of the wearer at the front emblem 22 and to the wearer at the rear by means of the rear emblem 23. Small adhesive means 15 are used in a multitude of locations on the rear emblem 23 and the front emblem 22. At a point approximately one third the length of the length portion 21 as measured from the front emblem 22 is placed a long adhesive means 24 which allows the user to adjust the length portion 21 as described further herein. The long adhesive means 24 is of similar material as the small adhesive means 15 but is meant to be adhered to the fabric comprising the length portion 21 as fully described below.

Figure 5:
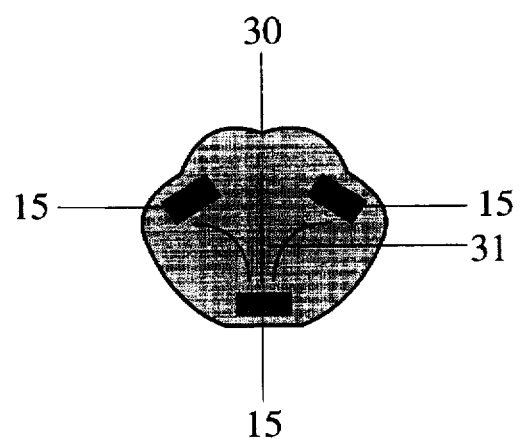
FIG. 5 shows the protective piece used to cover the sensitive portions of the breasts of a female.

FIG. 5 shows the breast cover 30 in reverse view, comprised of a breast emblem 31 kept on the wearer by a multitude of small adhesive means 15.

Figure 6:
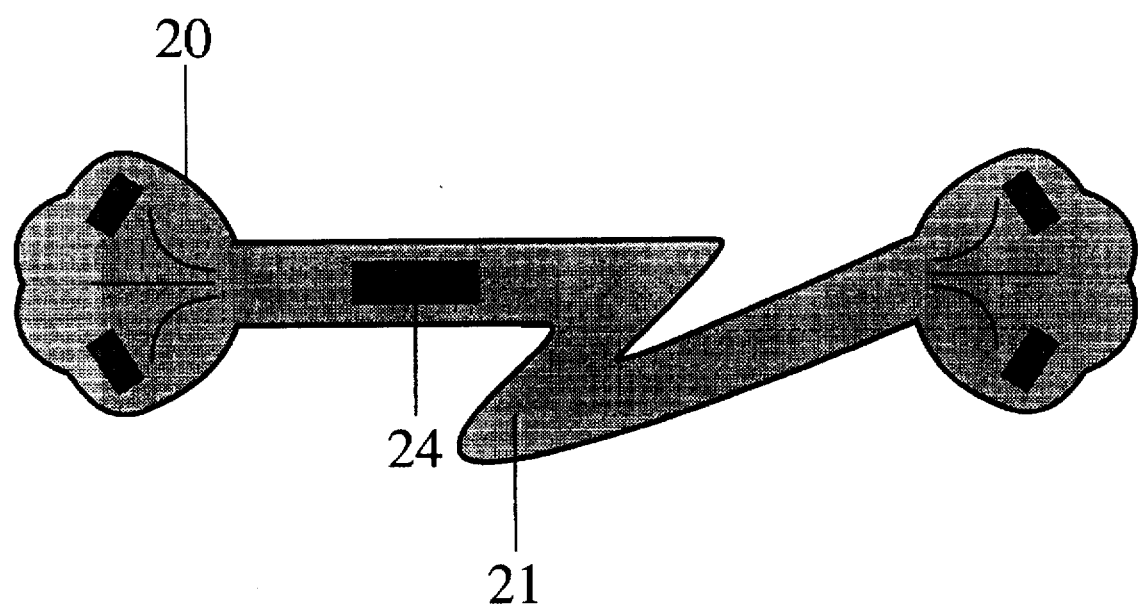
FIG. 6 shows the protective piece used to protect the genitalia area of a female in folded form whereby the length is fashioned to fit a smaller individual by folding.

FIG. 6 shows the lower cover 20 in folded view whereby the length portion 21 has been shortened by folding and secured by the long adhesive means 24, thereby providing a shorter adjusted length 25 for a smaller wearer.

Figure 7:
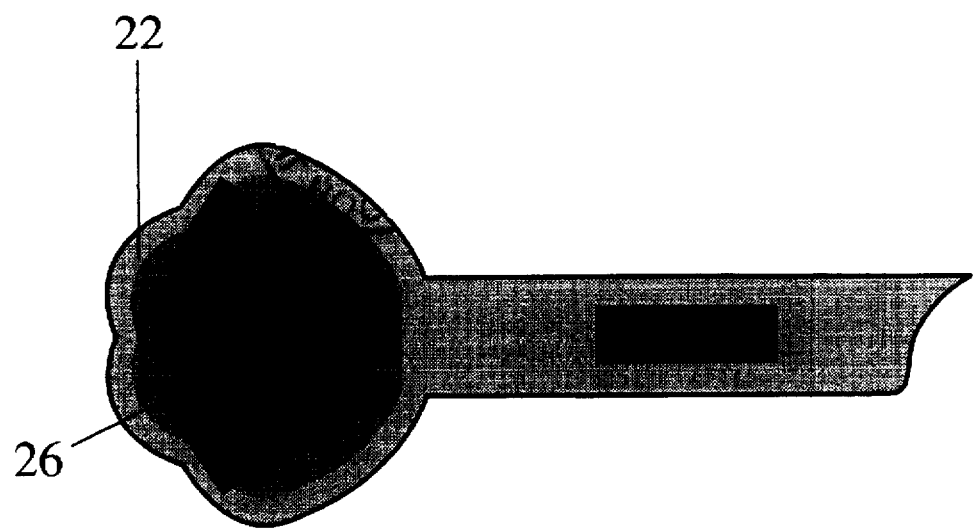
FIG. 7 shows a rear view of the front emblem having a pouch therein.
Figure 8:
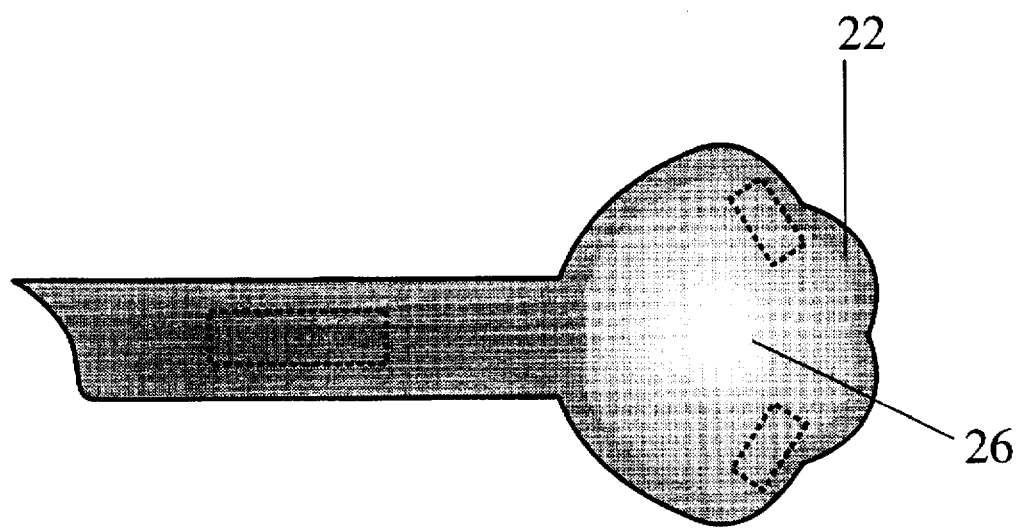
FIG. 8 shows a front view of the front emblem.

FIG. 7 shows the preferred embodiment for the male wearer from the rear view of the front emblem 22, having a pouch therein 26 to contain the male anatomy; and FIG. 8 shows the corresponding front view of the front emblem 22.

In the preferred embodiment for the male wearer, the front emblem is modified to include a back portion, which forms a pouch to accommodate the male anatomy within the front emblem.

What is claimed is:

1. A protective tanning kit for a wearer, comprising:
   a. a face mask, comprising:
      i. a face cover, made as an ovular shell of flexible, yet lightweight, opaque material having a front side and a reverse side and having an upper portion and a lower portion, and having two elliptical openings in said upper portion thereby forming openings for the wearer's eyes, and having a rectangular nose slit and a rectangular mouth slip in said lower portion with respect to said two elliptical openings;
      ii. two eye piece viewing means, each made as elliptical, opaque pieces being disposed within said respective elliptical openings; and,
      iii. a multitude of small adhesive means fastened to said face mask body reverse side whereby said small adhesive means are adhereable to said wearer;
   b. a pair of breast covers, each comprising a breast emblem, made as a pattern of flexible, yet lightweight, opaque material and having a front side and a reverse side and having a multitude of small adhesive means fastened to each breast cover on said reverse side, whereby said small adhesive means are adhereable to said wearer; and,
   c. a lower cover, comprising:
      i) a long rectangular length portion having a front side and a reverse side;
      ii) a front emblem at one end of said long rectangular length portion and a rear emblem at the opposing end of said long rectangular length portion, said front emblem and said rear emblem each having a front side and a reverse side and having small adhesive means in a multitude of locations on said reverse side of said rear emblem and on said reverse side of said front emblem;
      iii) a long adhesive means located on said reverse side of said long rectangular length portion at a point approximately one third the length of the long rectangular length portion as measured from the front emblem, whereby said wearer may adjust the long rectangular length portion to become shorter by folding said long rectangular length portion upon itself and be fixedly held by said long adhesive means.

2. A tanning kit as claimed in claim 1, further comprising small adhesive means formed from double backed adhesive paper whereby one backing of said double backed adhesive paper is adhered permanently to said face mask, to said lower portion and to said pair of breast covers and said opposite backing is adhered to said wearer and further comprising long adhesive means formed from double backed adhesive paper whereby one backing of said double backed paper is permanently adhered to said reverse side of said long rectangular portion and said opposite backing is adjustably adhered to said long rectangular length portion upon itself.

3. A tanning kit as claimed in claim 1, further comprising a lower portion for a male wearer, comprising a backing cover fastened to said reverse side of said front emblem of said lower cover whereby said male wearer is thereby provided protection.

* * * * *